United States Patent
Kesner

(10) Patent No.: US 11,006,919 B2
(45) Date of Patent: *May 18, 2021

(54) DATA DRIVEN METHODS FOR DERIVING AMPLITUDE-BASED MOTION CHARACTERIZATIONS IN PET IMAGING

(71) Applicant: The Regents of the University of Colorado, a body corporate, Denver, CO (US)

(72) Inventor: Adam Kesner, Denver, CO (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 16/840,544

(22) Filed: Apr. 6, 2020

(65) Prior Publication Data
US 2020/0352539 A1  Nov. 12, 2020

Related U.S. Application Data

(63) Continuation of application No. 15/753,586, filed as application No. PCT/US2016/049094 on Aug. 26, 2016, now Pat. No. 10,610,186.
(Continued)

(51) Int. Cl.
*A61B 6/00* (2006.01)
*A61B 6/03* (2006.01)
(Continued)

(52) U.S. Cl.
CPC ............ *A61B 6/5288* (2013.01); *A61B 5/055* (2013.01); *A61B 6/037* (2013.01); *A61B 6/5217* (2013.01);
(Continued)

(58) Field of Classification Search
None
See application file for complete search history.

(56) References Cited

U.S. PATENT DOCUMENTS 8,569,706 B2  10/2013  Thiruvenkadam et al.
10,610,186 B2 * 4/2020  Kesner .................. A61B 6/541
(Continued)

FOREIGN PATENT DOCUMENTS

WO  2014/141256 A1  9/2014

OTHER PUBLICATIONS

Dawood, Mohammad et al., "Respiratory Gating in Positron Emission Tomography: A Quantitative Comparison of Different Gating Schemes," Medical Physics, vol. 34, No. 7, pp. 3067-3076, Jul. 2007.
(Continued)

*Primary Examiner* — Leon Flores

(57) ABSTRACT

Various systems and methods for generating images are provided. In some embodiments, the techniques can include acquiring a medical image and an associated motion characterization. The motion characterization can then be used to generate a plurality of gated image data sets, sorted by phase in the motion cycle. A new amplitude-based motion characterization curve is derived from the association of phases with amplitude-based characteristics in the phase gated images. This newly derived amplitude-based motion characterization curve can then be used to re-sort data according to amplitude-based gating techniques known in the field or with data driven optimization techniques.

20 Claims, 15 Drawing Sheets

Related U.S. Application Data

(60) Provisional application No. 62/210,769, filed on Aug. 27, 2015.

(51) Int. Cl.

| | | |
|---|---|---|
| *G01R 33/565* | (2006.01) | |
| *G06T 11/00* | (2006.01) | |
| *G06T 7/262* | (2017.01) | |
| *G06T 7/73* | (2017.01) | |
| *G06T 7/246* | (2017.01) | |
| *A61B 5/055* | (2006.01) | |
| *A61B 8/08* | (2006.01) | |
| *G01R 33/563* | (2006.01) | |
| *G06K 9/62* | (2006.01) | |
| *G06T 7/269* | (2017.01) | |
| *G06K 9/32* | (2006.01) | |
| *G06T 3/40* | (2006.01) | |
| *G06T 7/60* | (2017.01) | |

(52) U.S. Cl.
CPC .......... *A61B 6/541* (2013.01); *A61B 8/5284* (2013.01); *G01R 33/56316* (2013.01); *G01R 33/56509* (2013.01); *G06K 9/6247* (2013.01); *G06K 9/6267* (2013.01); *G06T 7/248* (2017.01); *G06T 7/262* (2017.01); *G06T 7/74* (2017.01); *G06T 11/008* (2013.01); *A61B 6/5205* (2013.01); *G01R 33/56308* (2013.01); *G06K 9/3233* (2013.01); *G06T 3/40* (2013.01); *G06T 7/269* (2017.01); *G06T 7/60* (2013.01); *G06T 2207/10088* (2013.01); *G06T 2207/10104* (2013.01); *G06T 2207/10108* (2013.01); *G06T 2207/10132* (2013.01); *G06T 2207/20212* (2013.01); *G06T 2211/412* (2013.01)

(56) References Cited

U.S. PATENT DOCUMENTS

| | | |
|---|---|---|
| 2008/0265166 A1 | 10/2008 | Shekhar et al. |
| 2008/0273785 A1 | 11/2008 | Kesner |
| 2010/0260402 A1 | 10/2010 | Axelsson et al. |
| 2011/0116695 A1 | 5/2011 | Wollenweber et al. |
| 2012/0052010 A1 | 3/2012 | Sorensen et al. |
| 2012/0292534 A1 | 11/2012 | Geneser et al. |

OTHER PUBLICATIONS

International Application No. PCT/US2016/049094, International Search Report & Written Opinion, 9 pages, Nov. 10, 2016.

Jani, Shyam S. et al., "A Comparison of Amplitude-Based and Phase-Based Positron Emission Tomography Gating Algorithms for Segmentation of Internal Target Volumes of Tumors Subject to Respiratory Motion," Int J Radiat Oncol Biol Phys., vol. 87, No. 3, 15 pages, Nov. 1, 2013.

Liu, Chi et al., "Quiescent Period Respiratory Gating for PET/CT," Medical Physics, vol. 37, No. 9, pp. 5037-5043, Sep. 2010.

* cited by examiner

DATA DRIVEN METHODS FOR DERIVING AMPLITUDE-BASED MOTION CHARACTERIZATIONS IN PET IMAGING

CROSS-REFERENCE TO RELATED APPLICATIONS

This application is a continuation of U.S. patent application Ser. No. 15/753,586, filed Feb. 20, 2018, entitled "Data Driven Methods For Deriving Amplitude-Based Motion Characterizations In PET Imaging," and issued on Apr. 7, 2020 as U.S. Pat. No. 10,610,186, which claims the benefit of International Application No. PCT/US2016/049094, filed Aug. 26, 2016, entitled "Data Driven Methods For Deriving Amplitude Based Motion Characterizations In PET Imaging," which claims the benefit of U.S. Provisional Application No. 62/210,769, filed on Aug. 27, 2015, entitled "Data Driven Methods For Deriving Amplitude Based Motion Characterizations In PET Imaging," each of which is hereby incorporated by reference for all purposes in its entirety.

TECHNICAL FIELD

Various embodiments of the present invention generally relate to positron emission tomography. More specifically, some embodiments of the present invention relate systems and methods for data driven methods for deriving amplitude-based motion characterizations in positron emission tomography imaging.

BACKGROUND

Gating is a strategy for correcting cardiac and respiratory patient motion which occurs during medical imaging. Gating works by subjugating raw data into separate bins, which correlate with separate segments of the motion cycle. By applying such traditional gating techniques, systems are able to achieved improved resolution, but at the cost of image statistics.

Several methods have been proposed for sorting gated data in an "optimal" way. Because patient motion characterization traditionally comes in an amplitude vs time format, usually from a hardware based device, most strategies to date have either sorted raw data by amplitude, or time. More specifically, data is subjugated into gated data by separating it by its associated amplitude, or the phase (time between cycles) it was acquired at.

Both amplitude and phase based gating strategies have advantages and disadvantages. Amplitude-based strategies can be used to optimally segregate data, but they also suffer from drifting of hardware (changing baseline), are subject to instrument noise, and are less ideal to use with data driven motion characterization strategies. Phase-based gating can be more robust, and has advantages associated with equal segregation of statistics.

SUMMARY

Various systems and techniques for image generation are provided. In accordance with some embodiments, medical images and an associated motion characterization can be acquired (e.g., from a database or from an imaging system). The motion characterization can then used to generate a plurality of gated image data sets, sorted by phase in the motion cycle. A new amplitude-based motion characterization curve can be derived from the association of phases with amplitude-based characteristics in the phase gated images. This newly derived amplitude-based motion characterization curve can then be used to re-sort data according to amplitude-based gating techniques known in the field or with data driven optimization techniques presented here.

Embodiments of the present invention also include computer-readable storage media containing sets of instructions to cause one or more processors to perform the methods, variations of the methods, and other operations described herein.

Some embodiments can include acquiring a set of phase gated medical images of a patient collected via a medical imaging procedure (e.g., positron emission tomography, magnetic resonance imaging, ultrasound, single-photon emission computed tomography, or planar gamma camera imaging). A principal component analysis can be applied across phases of the set of phase gated medical images to generate an phase-motion amplitude curve describing an amplitude of motion of a patient during the medical imaging procedure as a function of phase of a periodic motion cycle. In some embodiments, the phase-motion amplitude curve is based on the first principal component. An acceptance window can be identified based on variations in the non-first principal component fluctuations. Then, an optimal segregation of image data can be determined based on the phase-motion amplitude curve. Single medical images can then be generated based on the optimal segregation of the image data.

In some embodiments, determining optimal segregation of the image data can include analyzing each point on the phase-motion amplitude curve to assess how many other curve data points are within the acceptance window. In addition, determining the optimal segregation can include classifying each image based on placement on the phase-motion amplitude curve and grouping medical images from the set of medical images based on the classification. A position of the patient within each medical image in the set of medical images can be characterized in some embodiments by using one or more of a correlative measure or a signal displacement measure.

In some embodiments, a set of phase gated medical images of a patient collected via a medical imaging procedure can be acquired. By applying a principal component analysis of the set of medical images, an indication of amplitude fluctuations across the phases representing motion of the patient during the medical imaging procedure can be generated. The principal component analysis of the set of images includes identifying a set of pixels across each medical image in the set of medical images representing a common point of interest. Motion of the patient can be characterized based on the indication of phase and amplitude fluctuations.

In some embodiments, the indication of phase and amplitude fluctuations can be analyzed to determine optimal bin sizes for sorting the set of medical images to maximize image resolution. Then, a set of gated medical images can be generated based on sorting of image data. In some embodiments, the set of gated medical images may only be generated when the image resolution is improved by at least a set threshold of detected motion.

Some embodiments provide for a system comprising a memory, one or more processors, an image acquisition module, a motion characterization module, an optimization module, and an image processing module. Some embodiment may include other components or machines, such as but not limited to imaging systems (e.g., a positron emission tomography machine, a magnetic resonance imaging machine, an ultrasound machine, a single-photon emission computed tomography machine, or a planar gamma camera imaging machine.) The image acquisition module can be configured to acquire a set of medical images of a patient collected via a medical imaging procedure. The motion characterization module can be configured to characterize gating motion of the patient based on the set of medical images. The optimization module can be configured to determine optimal bin sizes that maximize image resolution. The image processing module, under the control of the processor, can be configured to generate a set of gated medical images by sorting the set of medical images into bins based on the optimal bin sizes and combining medical images within each of the bins to create the set of gated medical images.

In some embodiments, the motion characterization module can apply a principal component analysis of the set of medical images to generate an indication of phase and amplitude fluctuations representing gating of the patient during the medical imaging procedure. The motion characterization module may be further configured to identify a center of mass measurement, calculate a gradient displacement, or a minimize a cost function or characterize a position of the patient within each medical image in the set of medical images by using one or more of a correlative measure, a signal displacement measure, or a principal component analysis. The correlative measure can include a Pearson correlation or a mutual information correlation and the signal displacement measure is based on a center of mass.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the scope of the present invention. Accordingly, the drawings and detailed description are to be regarded as illustrative in nature and not restrictive.

BRIEF DESCRIPTION OF THE DRAWINGS

Embodiments of the present technology will be described and explained through the use of the accompanying drawings in which.

Figure 1:
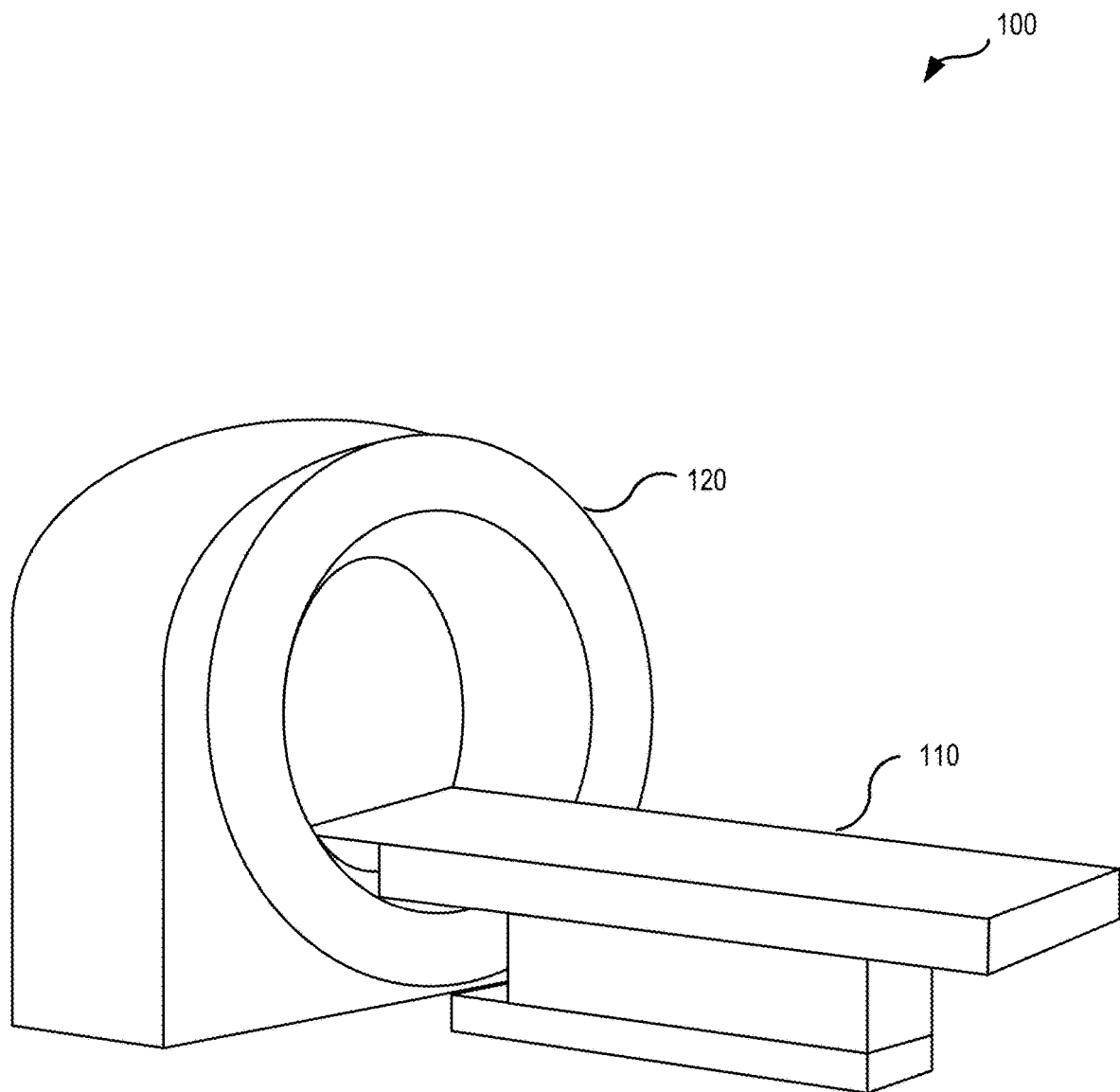
FIG. 1 illustrates an example of an imaging system in which some embodiments of the present technology may be utilized.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Respiratory gating is a strategy for correcting cardiac and respiratory motion patient motion in PET imaging. To implement gating, there first must be a characterization of the patient's motion, which can be provided by hardware or software devices. However, these motion characterizations do not always correlate with internal motion (i.e. the relevant signal).

Motion characterization can be used to gate data, using either phase-based subjugation of data (e.g. in the time domain), or by amplitude-based methods (e.g. in the motion amplitude domain). Often phase-based gating is easier and more robust, but it has been shown that amplitude-based gated images may be more useful clinically.

Various embodiments of the present invention use the information in the phase-based subjugated data to characterize an amplitude motion model. In some embodiments, an initial motion characterization can be used to sort image data into phase gated data sets, containing images that span the phases of a periodic cycle (e.g., a cardiac cycle, a respiratory cycle, etc.). A secondary, amplitude representative motion characterization can then be derived from the phase gated image data set, through use of fluctuation data drive correlative measures (e.g., principal component analysis, Pearson correlation, mutual information, etc.) or with signal displacement measures (e.g., center of mass) measured at each phase. The resultant data driven amplitude motion characterization then describes the relationship between phases of the periodic cycle and the extracted data driven amplitude values. This defined relationship can then be used to convert an initial motion characterization defined in time-phase dimensions to a new motion characterization defined in time-data driven amplitude dimensions.

The motion characterization defined in time-data driven amplitude dimensions can then be used for amplitude-based gating, or optimal period of data determination and reconstruction, as is described in literature. In another embodiment, the processes can be used to both generate an amplitude-based motion characterization, as well as a time dependent strength of correlation measure, which can be used to determine the optimal segments of data to be utilized.

In the following description, for the purposes of explanation, numerous specific details are set forth in order to provide a thorough understanding of embodiments of the present invention. It will be apparent, however, to one skilled in the art that embodiments of the present invention may be practiced without some of these specific details. For example, while some embodiments use gated PET data, other embodiments extend to other imaging modalities, such as, but not limited to, SPECT, MRI, ultrasound, etc.

Moreover, the techniques introduced here can be embodied as special-purpose hardware (e.g., circuitry), as programmable circuitry appropriately programmed with software and/or firmware, or as a combination of special-purpose and programmable circuitry.

Hence, embodiments may include a machine-readable medium having stored thereon instructions that may be used to program a computer (or other electronic devices) to perform a process. The machine-readable medium may include, but is not limited to, floppy diskettes, optical discs, compact disc read-only memories (CD-ROMs), magneto-optical discs, ROMs, random access memories (RAMs), erasable programmable read-only memories (EPROMs), electrically erasable programmable read-only memories (EEPROMs), application-specific integrated circuits (ASICs), magnetic or optical cards, flash memory, or other type of media/machine-readable medium suitable for storing electronic instructions.

Terminology

Brief definitions of terms, abbreviations, and phrases used throughout this application are given below.

The phrases "in some embodiments," "according to some embodiments," "in the embodiments shown," "in other embodiments," and the like generally mean the particular feature, structure, or characteristic following the phrase is included in at least one implementation of the present invention, and may be included in more than one implementation. In addition, such phrases do not necessarily refer to the same embodiments or different embodiments.

If the specification states a component or feature "may", "can", "could", or "might" be included or have a characteristic, that particular component or feature is not required to be included or have the characteristic.

The term "module" refers broadly to a software, hardware, or firmware (or any combination thereof) component. Modules are typically functional components that can generate useful data or other output using specified input(s). A module may or may not be self-contained. An application program (also called an "application") may include one or more modules, or a module can include one or more application programs.

General Description

FIG. 1 illustrates an example of imaging system 100 in which some embodiments of the present technology may be utilized. Imaging system 100 can be any system capable of collecting medical images, such as but not limited to a positron emission tomography machine, a magnetic resonance imaging machine, an ultrasound machine, a single-photon emission computed tomography machine, or other machine. A patient can be positioned on the moveable platform or bed 110 that can move to place the patient within the detection mechanism 120. Imaging system 100 can then scan portions of the patient (i.e., regions of interest) to create sets of medical images. In some embodiments, imaging system 100 may include one or more motion sensors to detect motion of the patient (e.g., cardiac or respiratory motion). The set of medical images, motion information, and/or other data may be stored within a database (not shown) for retrieval and processing.

Figure 2:
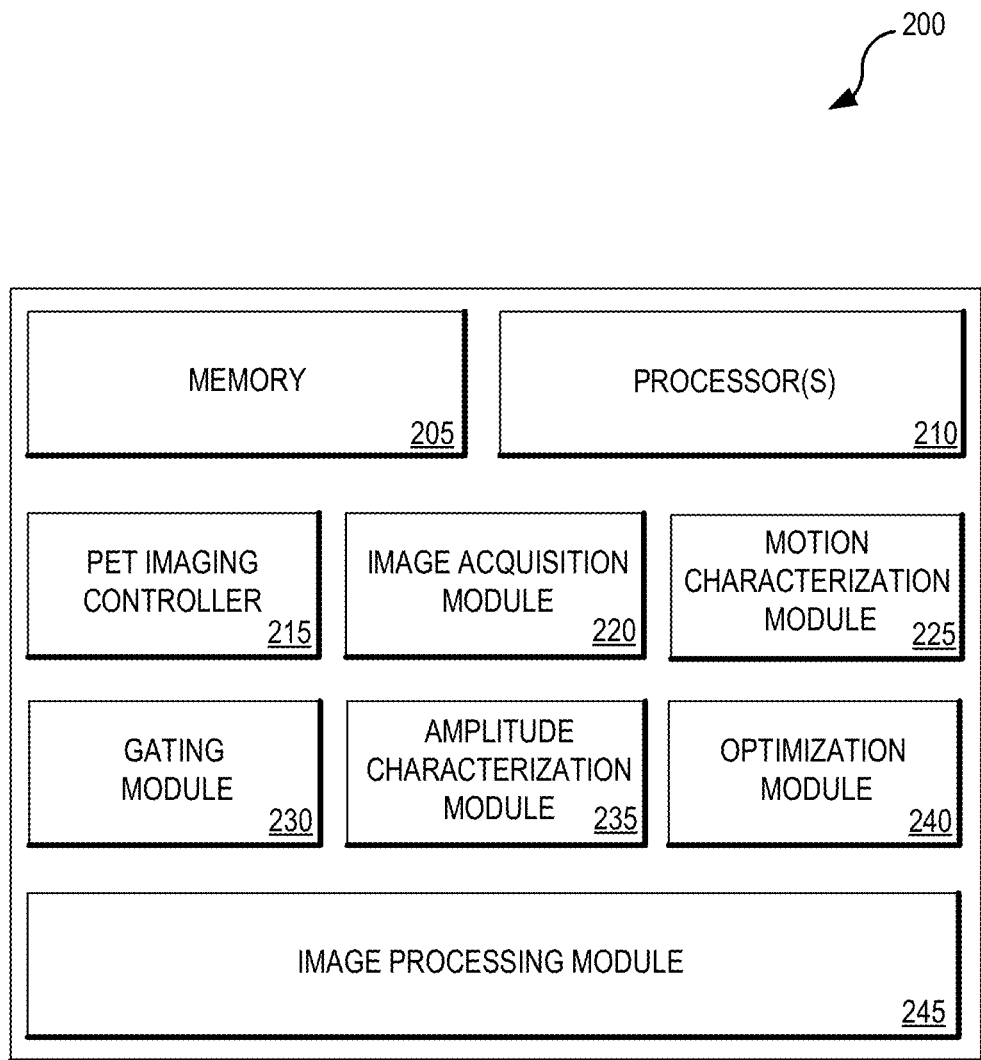
FIG. 2 illustrates a set of components within an image processing device according to one or more embodiments of the present technology.

FIG. 2 illustrates a set of components within an image processing device according to one or more embodiments of the present technology. According to the embodiments shown in FIG. 2, image processing device 200 can include memory 205, one or more processors 210, PET imaging controller 215, image acquisition module 220, motion characterization module 225, gating module 230, amplitude characterization module 235, optimization module 240, and image processing module 245. Each of these modules can be embodied as special-purpose hardware (e.g., one or more ASICS, PLDs, FPGAs, or the like), or as programmable circuitry (e.g., one or more microprocessors, microcontrollers, or the like) appropriately programmed with software and/or firmware, or as a combination of special purpose hardware and programmable circuitry. Other embodiments of the present technology may include some, all, or none of these modules and components along with other modules, applications, and/or components. Still yet, some embodiments may incorporate two or more of these modules and components into a single module and/or associate a portion of the functionality of one or more of these modules with a different module. For example, in one embodiment, image processing device 200 may include a graphical user interface (GUI) generation module to generate one or more GUI screens that allow a user to review and/or select various settings or options.

Memory 205 can be any device, mechanism, or populated data structure used for storing information. In accordance with some embodiments of the present technology, memory 205 can encompass any type of, but is not limited to, volatile memory, nonvolatile memory and dynamic memory. For example, memory 205 can be random access memory, memory storage devices, optical memory devices, media magnetic media, floppy disks, magnetic tapes, hard drives, SDRAM, RDRAM, DDR RAM, erasable programmable read-only memories (EPROMs), electrically erasable programmable read-only memories (EEPROMs), compact disks, DVDs, and/or the like. In accordance with some embodiments, memory 205 may include one or more disk drives, flash drives, one or more databases, one or more tables, one or more files, local cache memories, processor cache memories, relational databases, flat databases, and/or the like. In addition, those of ordinary skill in the art will appreciate many additional devices and techniques for storing information which can be used as memory 205.

Memory 205 may be used to store instructions for running one or more applications or modules on processor(s) 210. For example, memory 205 could be used in one or more embodiments to house all or some of the instructions needed to execute the functionality of PET imaging controller 215, image acquisition module 220, motion characterization module 225, gating module 230, amplitude characterization module 235, optimization module 240, and/or image processing module 240. Memory 205 may also include an operating system that provides a software package that is capable of managing the hardware resources and provide common services for software applications running on processor(s) 210.

Imaging controller 215 can be configured to communicate with and generate commands to control an imaging system to scan a region of interest of a patient. The images can be stored in a database or processed in real-time (or near real-time) before being stored in the database. Image acquisition module 220 can be configured to acquire the set of medical images of a patient collected via the medical imaging procedure. The image acquisition can include, for example, the retrieval of the images from the database or management of the real-time (or near real-time) processing.

Motion characterization module 225 can be used to characterize patient motion during scan acquisition. Motion characterization may be acquired using external hardware, or data driven strategies. Gating module 230 can sort acquisition data relative to the phases derived from the motion characterization to generate phase gated data sets.

The amplitude characterization module 235 will derive a characterization of the amplitude of patient motion as a function of the phases of motion using data driven metrics. In some embodiments, amplitude characterization module 235 can apply a principal component analysis of the set of medical images to generate an indication of amplitude fluctuations representing motion of the patient during the medical imaging procedure. In addition, some embodiments of amplitude characterization module 235 can identify a center of mass measurement, calculate a gradient displacement, or a minimized cost function, relative to the phases of the gated cycle.

Optimization module 240 can be configured to determine optimal bin boundaries that maximize final image resolution. The characterization of the amplitude of patient motion generated with the amplitude characterization module 235 can be processed to determine the optimal bin boundaries. Image processing module 245 can then generate an optimal image or a set of optimally gated images by resorting the image data 220 relative to the optimal bin boundaries.

Figure 3:
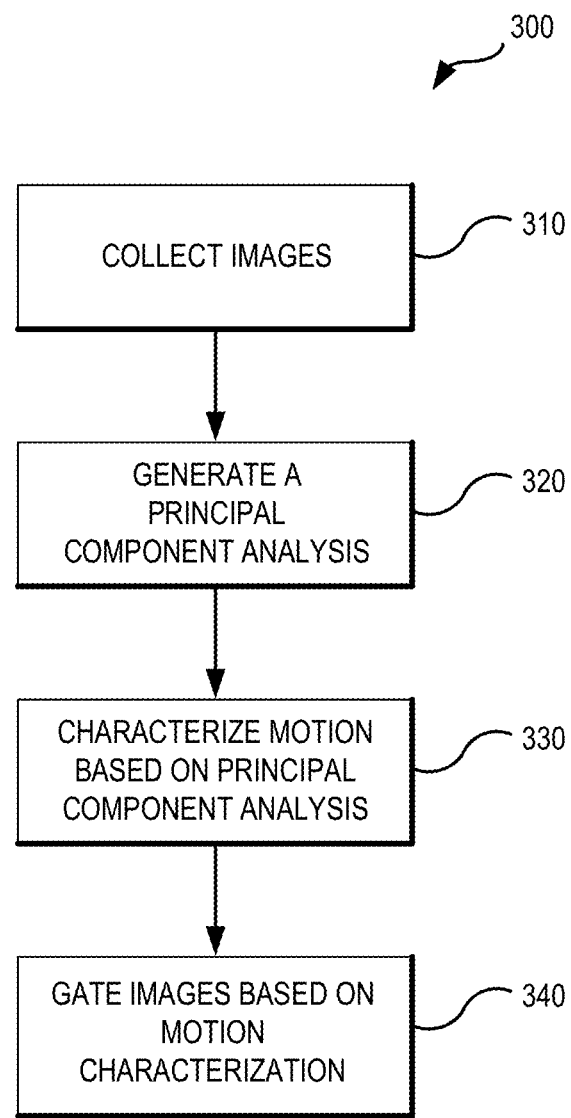
FIG. 3 is a flowchart illustrating a set of operations for generating gated images according to one or more embodiments of the present technology.

FIG. 3 is a flowchart illustrating a set of operations 300 for generating gated images according to one or more embodiments of the present technology. As illustrated in FIG. 3, during collection operation 310 a set of images (e.g., medical images) are collected. This set of images may be retrieved from a database on which the images are stored, collected directly from the imaging system, or from some other source. Once the set of images have been collected, analysis operation 320 is used to generate a principal component analysis which is a statistical procedure that uses an orthogonal transformation to convert a set of observations of possibly correlated variables into a set of values of linearly uncorrelated variables called principal components. Various implementation techniques can be used to efficiently generate the principal component analysis. The following document is incorporated by reference herein for all purposes: "A tutorial on Principal Components Analysis," by Lindsay I. Smith, Feb. 26, 2002.

Using the results from the principal component analysis, motion of the patient can be characterized from the images during characterization operation 330. Using this motion characterization, gating operation 340 can be used to generated gated images based on the motion characterization. For example, in some embodiments, a weight factor array of the first principal component can be used to define phase motion amplitude relationship (see FIGS. 9 and 10). Using a weighted factor array of second, third and/or fourth principal components to define amplitude of non-first principal component fluctuations phase motion amplitude relationship. The variations in the non-first principle component fluctuations can be used to scale an "acceptance window", that will define how close points on the first principle component phase motion amplitude can be to be identified as "similar." For example, an acceptance window may be defined as ±3 standard deviations non first principle component fluctuations (see, e.g., FIG. 12).

Each point on the phase-motion amplitude curve (defined from first principal components) can be analyzed to assess how many other curve data points are within the amplitude acceptance window and can be classified as similar. Whichever point has the most "similar" adjacent points then the phase corresponding to that point, and the other phases classified as "similar", and the data corresponding to those phases can be grouped together to form a single optimal data set. In accordance with some embodiments, if multiple points are tied for most similar adjacent points, either can be used. In addition, it is possible for all points to be "similar", indicating that the phase motion amplitude relationship is non-significant and 100% of data should be binned together. Similarly, it is possible for no points to be similar, indicating that the phase motion amplitude relationship contained a significant amount of motion, and that it is optimal not to group similar data. Final images can then be created from optimal grouping of data sets.

Figure 4:
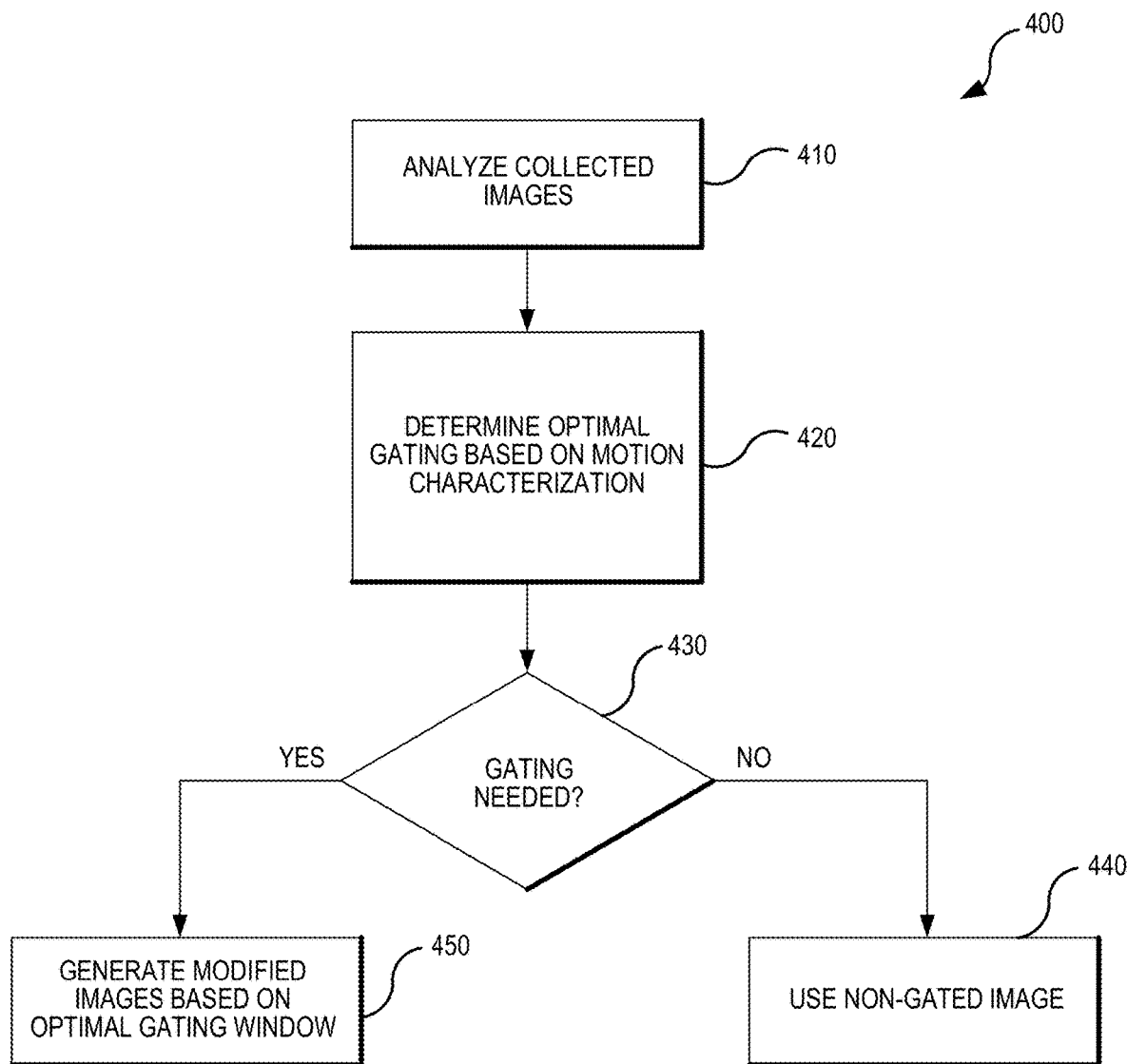
FIG. 4 is a flowchart illustrating a set of operations for analyzing images according to one or more embodiments of the present technology.

FIG. 4 is a flowchart illustrating a set of operations 400 for analyzing images according to one or more embodiments of the present technology. As illustrated in FIG. 4, analysis operation 410 analyzes the collected images characterize motion within a set of images. In accordance with various embodiments, this can be done by generating a data driven amplitude-based motion characterization curve. This amplitude-based curve can be derived from amplitude characteristics with phase gated data. Using this information, determination operation 420 can identify an arrangement for optimally segregating data into gated images, or a single optimal image. Using the information determination operation 430 can determine if any gating is needed. When determination operation 430 determines that no gating is needed then return operation 440 returns the non-gated images for use. When determination operation 430 determines that gating will be beneficial (e.g., to improve image quality), then gating operation 430 branches to generation operation 450 where modified images are generated based on optimal window gating.

To implement gating, medical images must be acquired along with a characterization of patient motion. This initial characterization is provided by hardware or software (data driven gating) devices. Motion characterization can be used to gate data, using either phase-based subjugation of data (e.g. in the time domain), or by amplitude-based methods (e.g. in the motion amplitude domain). Often phase-based gating is easier and more robust, but it has been shown that amplitude-based gated images may be more useful clinically.

Because amplitude of motion and phase of motion correlate with the same periodicity, some embodiments are able to associate the two in a single set of data. As a result, information in the phase-based subjugated data can be used to derive an amplitude motion characterization. Specifically, some embodiments first generate an initial characterization of the gated data set representing the entire periodic cycle (cardiac, respiratory). This initial characterization is constructed using traditional phase-based gating methodology. A new amplitude-based motion characterization can then be derived from amplitude/correlative measures on the phase subjugated data, or through correlation of subsets of raw data with phase subjugated data. The new amplitude-based motion characterization may then be used to subjugate data into amplitude-based gating bins, or an optimal single bin, as described in literature.

In some embodiments, the quality of the amplitude-based signal and/or motion is evaluated, and used to determine optimal final segregation of data (1-n bins). For example, poorly defined amplitude motion characterization may indicate non-gated image data as optimal. In other embodiments, the optimal final segregation of data can be derived using statistical modelling to determine the expected variations for the data set's amplitude or correlative characterization. Data can then be sorted relative to its amplitude (or correlative characterization) as well as its dependability from its separation from random fluctuations, derived from the statistical modelling. Data can be sorted in either pre reconstructed format and then reconstructed or post reconstructed format.

In various embodiments, the optimal final segregation of data is derived by comparing the amplitude curves from correctly and incorrectly sorted data. Correctly sorted data (structured data set) is derived from phase-based data segregation. Incorrectly sorted data (random data set) can be derived by random subjugation of data. Optimal final segregation of data will be derived relative to its amplitude (or correlative) characterization, as described by the structured data set, as well as its dependability derived from the comparison of structured and random curves. This process and example scenarios are described in more detail below.

Figure 5:
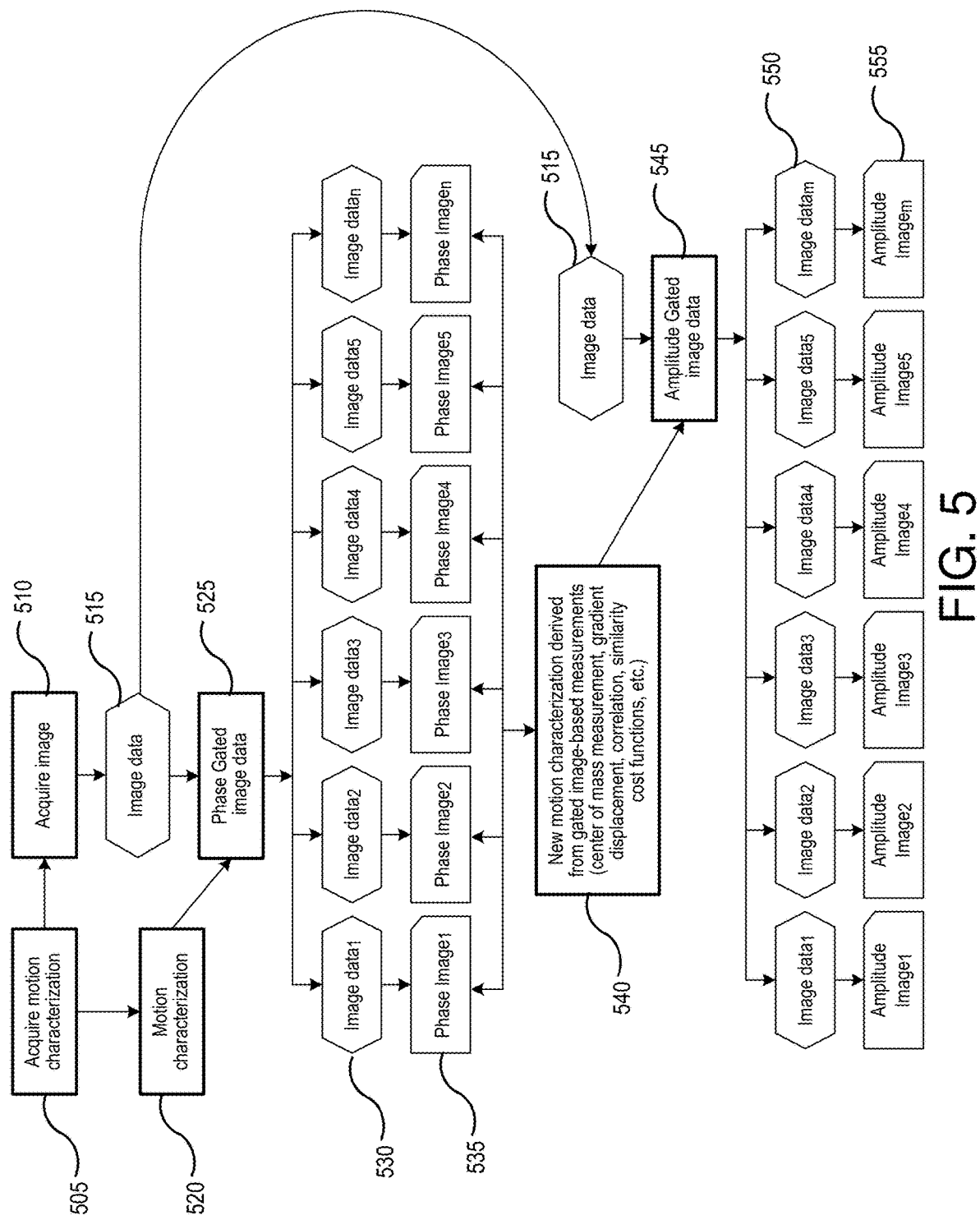
FIG. 5 is a flowchart illustrating a set of operations for generating an amplitude motion characterization curve and amplitude-based images through characterization of amplitude properties on phase gated data sets in accordance with some embodiments of the present technology.

FIG. 5 is a flowchart illustrating a set of operations 500 for generating an amplitude motion characterization curve and amplitude-based images through characterization of amplitude properties on phase gated images in accordance with some embodiments of the present technology. As illustrated in FIG. 5, acquisition operation 505 acquires motion characterization data along with the image acquisition operation 510. Raw imaging data 515 can be segmented into a phase gated data set based on the motion characterization 520 of the patient. The phase gated data set 530 can be sorted into bins 530 and reconstructed into image 535 which can then be used by derivation operation 540 to create a new motion characterization derived from the gated images based measurements (e.g., center of mass measurement, gradient displacement, correlation, similarity, cost functions, etc.). Using the new motion characterization along with image data 515, amplitude gated image data set 545 can be generated and separated into bins 550 and amplitude gated images 555.

In accordance with various embodiments, amplitude characterization can be derived through representative amplitude measures: center of mass displacement, optical flow, boundary motion, etc. Amplitude characterization can be derived, in some embodiments through correlative measures, e.g. correlations between short time data and phase gated data, phase gated data and phase gated data, phase gated data and summed data, phase gated data and subsets of phase gated data. Amplitude characterization of data can, in accordance with various embodiments, take place in both pre-reconstructed space and post reconstructed space.

Figure 6:
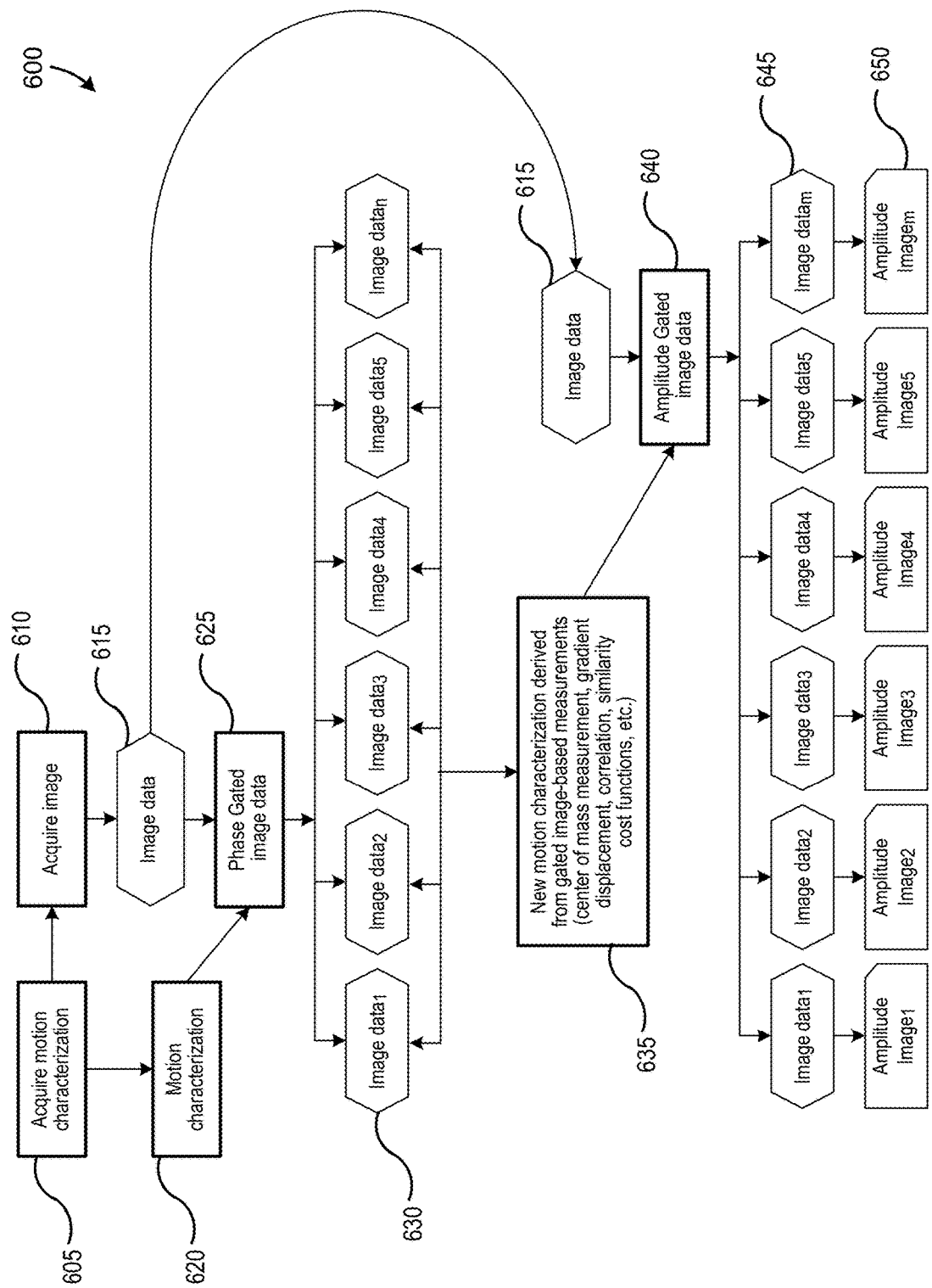
FIG. 6 is a flowchart illustrating a set of operations for generating an amplitude motion characterization curve and amplitude-based images through characterization of amplitude properties on phase gated images in accordance with one or more embodiments of the present technology.

FIG. 6 is a flowchart illustrating a set of operations 600 for generating an amplitude motion characterization curve and amplitude-based images through characterization of amplitude properties on phase gated images in accordance with some embodiments of the present technology. As illustrated in FIG. 6, acquisition operation 605 acquires motion characterization data along with the image acquisition operation 610. Raw imaging data 615 can be segmented into a phase gated images based on the motion characterization 620 of the patient. The phase gated image set 630 can be used by derivation operation 635 to create a new motion characterization derived from the gated images based measurements (e.g., center of mass measurement, gradient displacement, correlation, similarity, cost functions, etc.). Using the new motion characterization along with image data 615, amplitude gated image data set 640 can be generated and separated into bins 645 and amplitude gated images 650.

Figure 7:
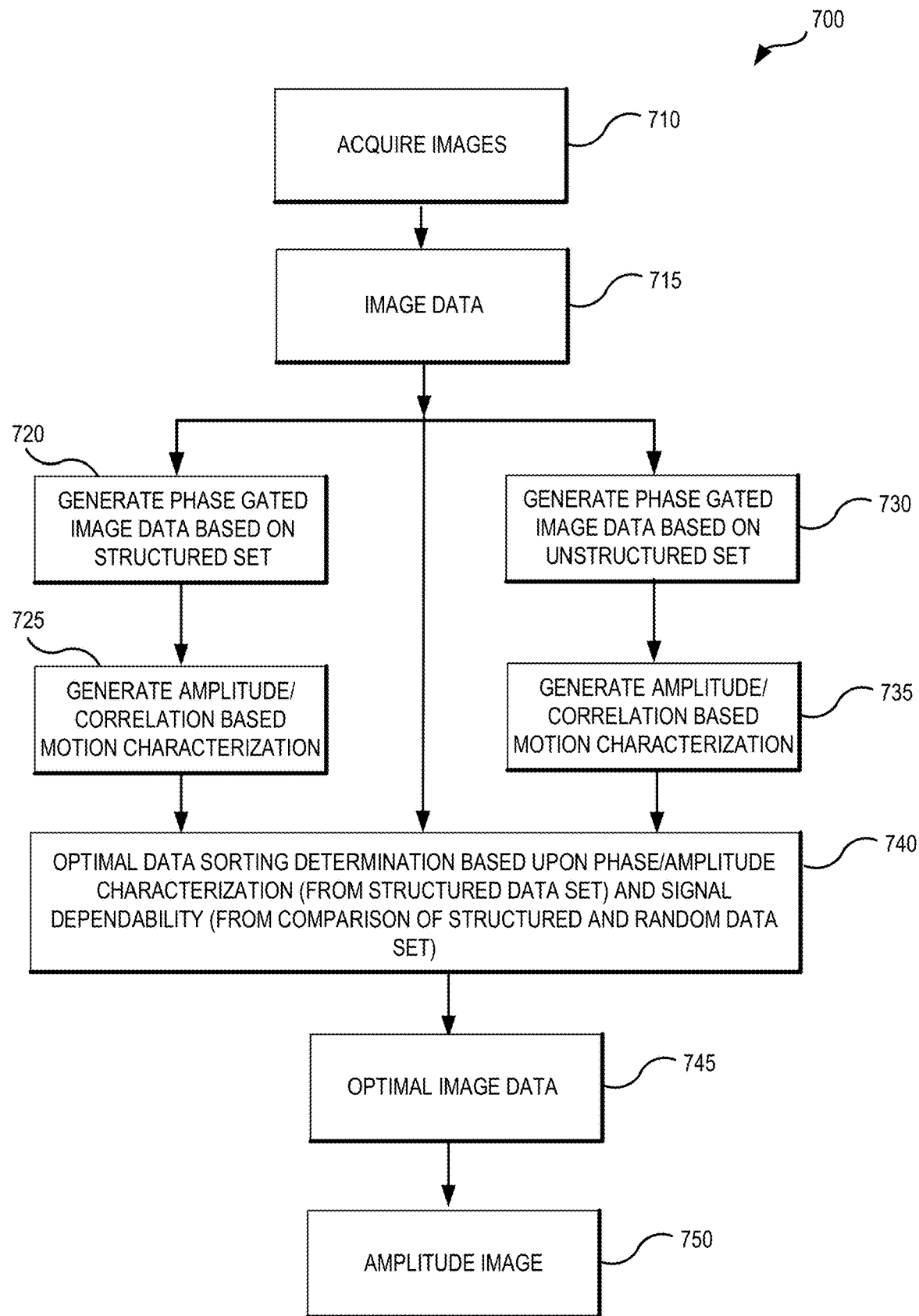
FIG. 7 is a flowchart illustrating a set of operations for segregation of data using structured data sets and random data sets in accordance with some embodiments of the present technology.

FIG. 7 is a flowchart illustrating a set of operations 700 for segregation of data using structured data sets and random data sets in accordance with some embodiments of the present technology. As illustrated in FIG. 7, acquisition operation 710 can acquire images and processed to generate image data 715. Processing operation 720 can generate phase gated image data based on a structured set. Then, characterization operation 725 can generated an amplitude/correlation based motion characterization. In addition, from image data 715, phase gated image data can be generated on an unstructured set during processing operation 730. Then, using these phase gated images, characterization operation 735 can generate an amplitude/correlation based motion characterization. Both of the motion characterization are used by sorting operation 740 to optimally sort the data based upon the characterizations from the structured data set and signal dependability from a comparison of the structured and unstructured (e.g., random) data sets. Using the optimal sorting, the image data can be created in imaging operation 745 along with amplitude images 750.

Figure 8:
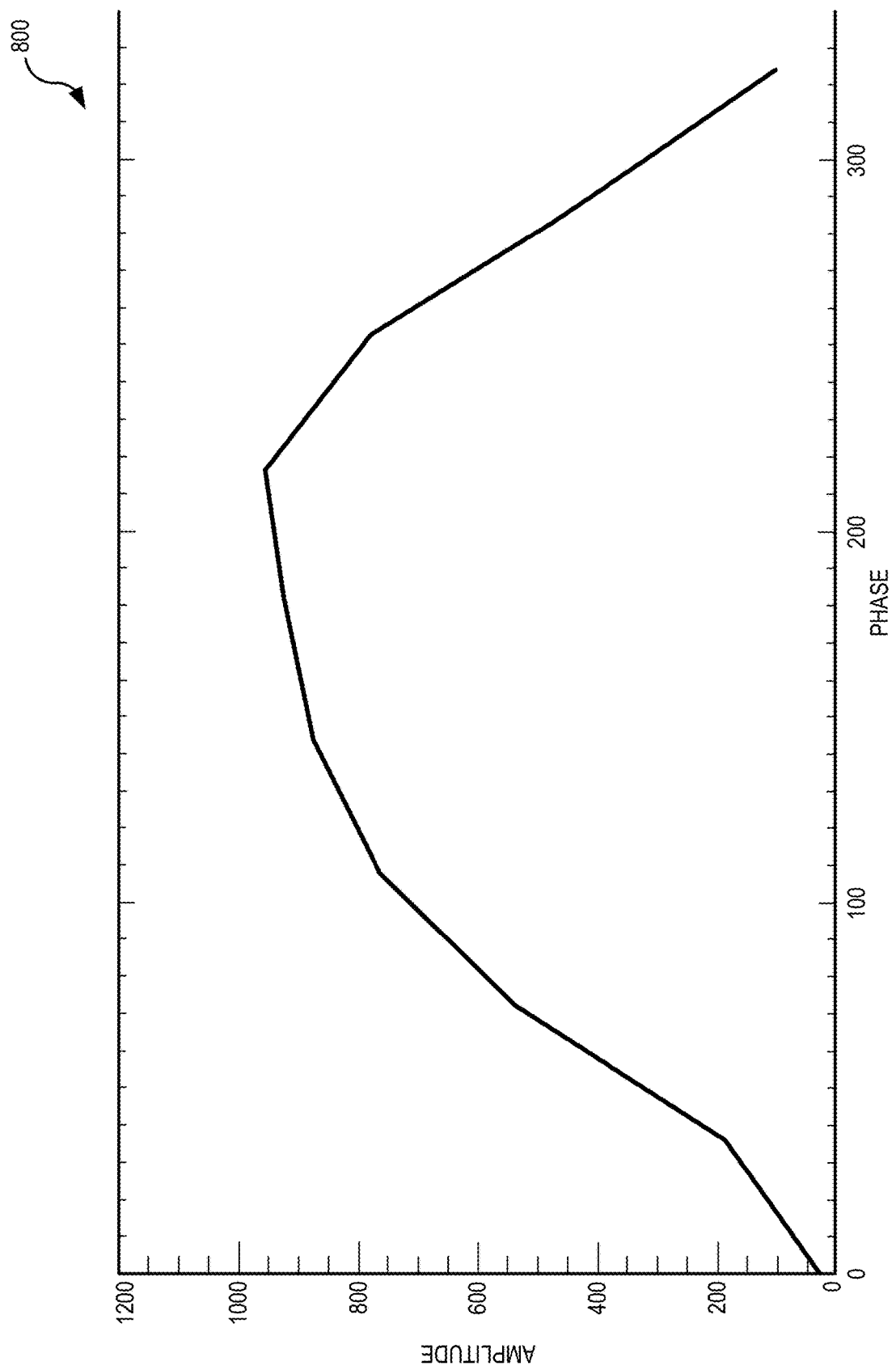
FIG. 8 illustrates a data driven motion curve from a patient with significant motion in accordance with various embodiments of the present technology.
Figure 9:
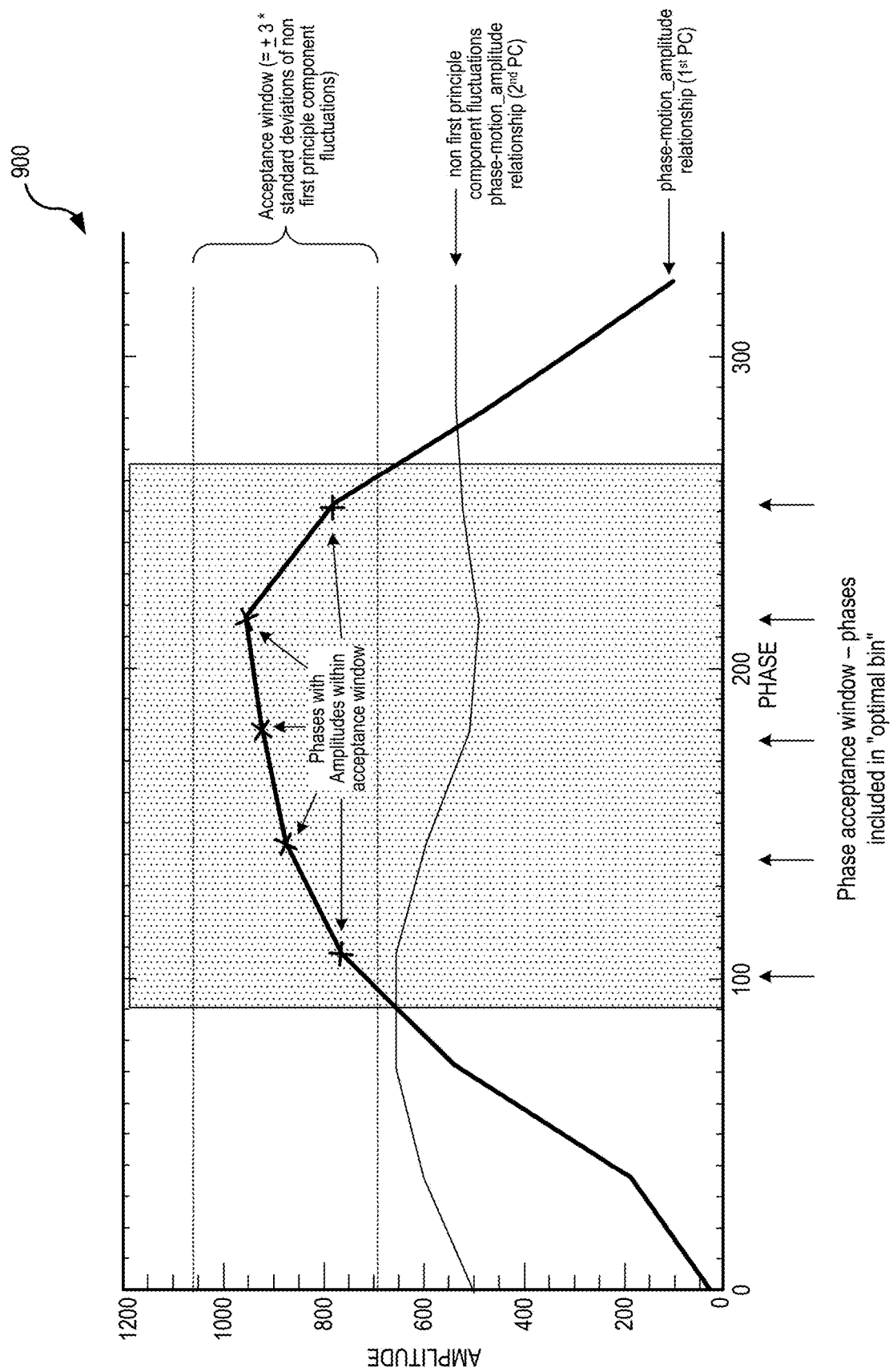
FIG. 9 illustrates a data drive motion curve and optimal phase acceptance window according to one or more embodiments of the present technology.

FIG. 8 illustrates a data driven motion curve from a patient with significant motion in accordance with various embodiments of the present technology. This is an example of a derivation of amplitude-based motion characterizations derived using displacement or correlative measures. These characterizations are referred to as phase-amplitude transfer functions. Once the data driven amplitude phase characterization curve is created, an optimal phase acceptance window can be selected as illustrated in FIG. 9.

Figure 10:
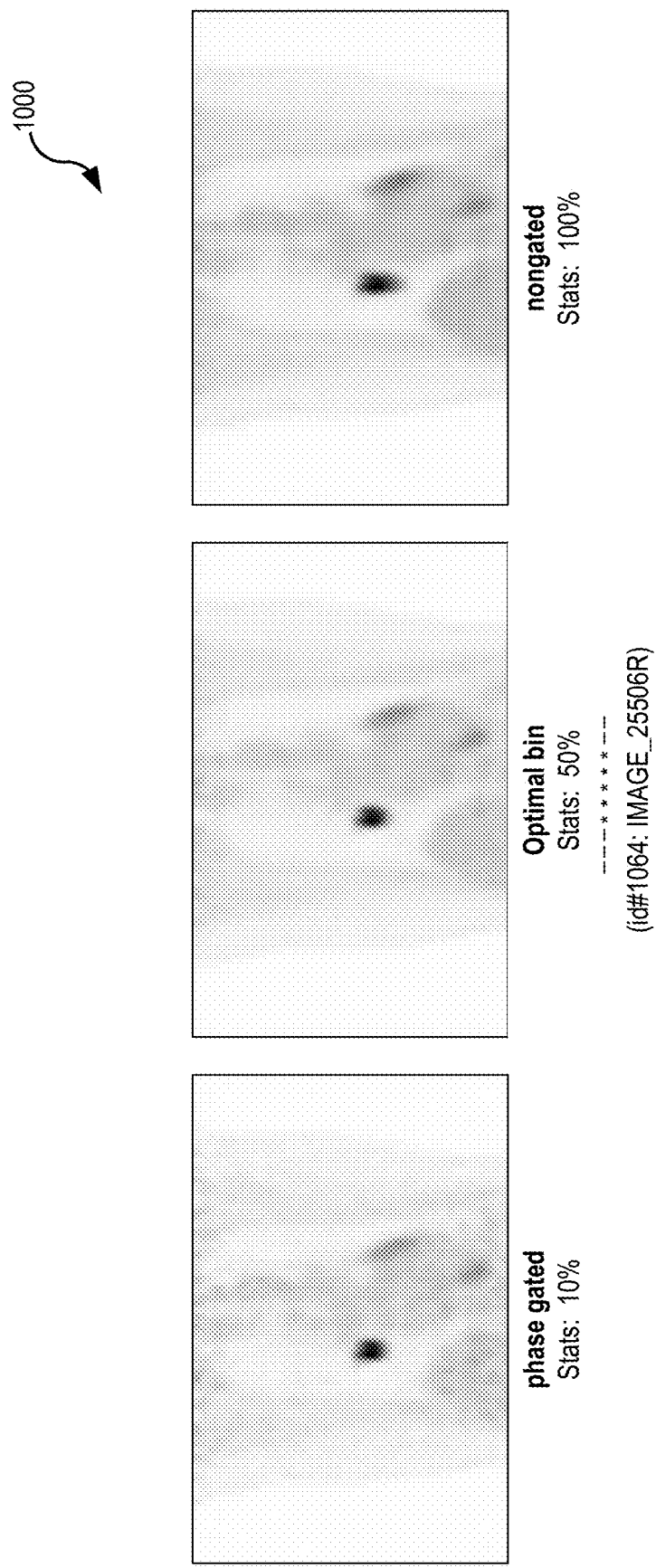
FIG. 10 illustrates images derived from signal binned, optimal binned, and fully binned data in accordance with various embodiments of the present technology.

Using the amplitude phase characterization curve and associated image data set, a determination can be made of which portions of the phase gated data set are ideal to combine to create a single optimal non-gated image instance. For example, the phase acceptance window may be selected window where amplitude above or below threshold. The threshold may be defined from curve (e.g. 35% of global amplitude shift) or by other image based metrics (fluctuations in principle component weight vectors). The data can then be sorted and combined relative to window selection. Using the sorting based on the acceptance window, derived images can be created. FIG. 10 illustrates images derived from signal binned, optimal binned, and fully binned data in accordance with various embodiments of the present technology. In some embodiments, the image generated with optimal segregation of data can makes use of gated information (i.e. improved resolution) while minimizing count statistics lost through data segregation.

Figure 11:
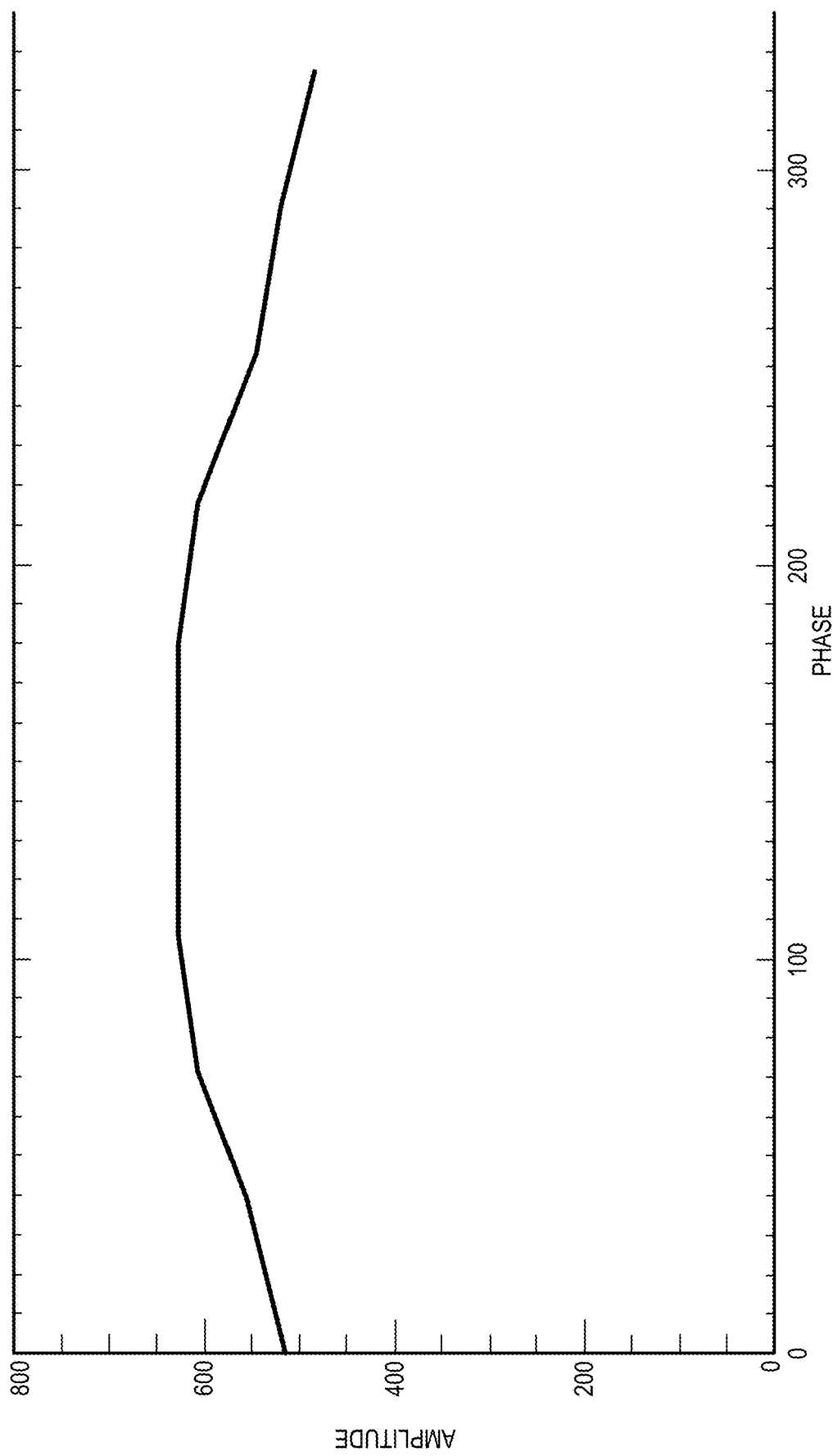
FIG. 11 illustrates a data driven motion curve from a patient with non-significant motion in accordance with various embodiments of the present technology.
Figure 12:
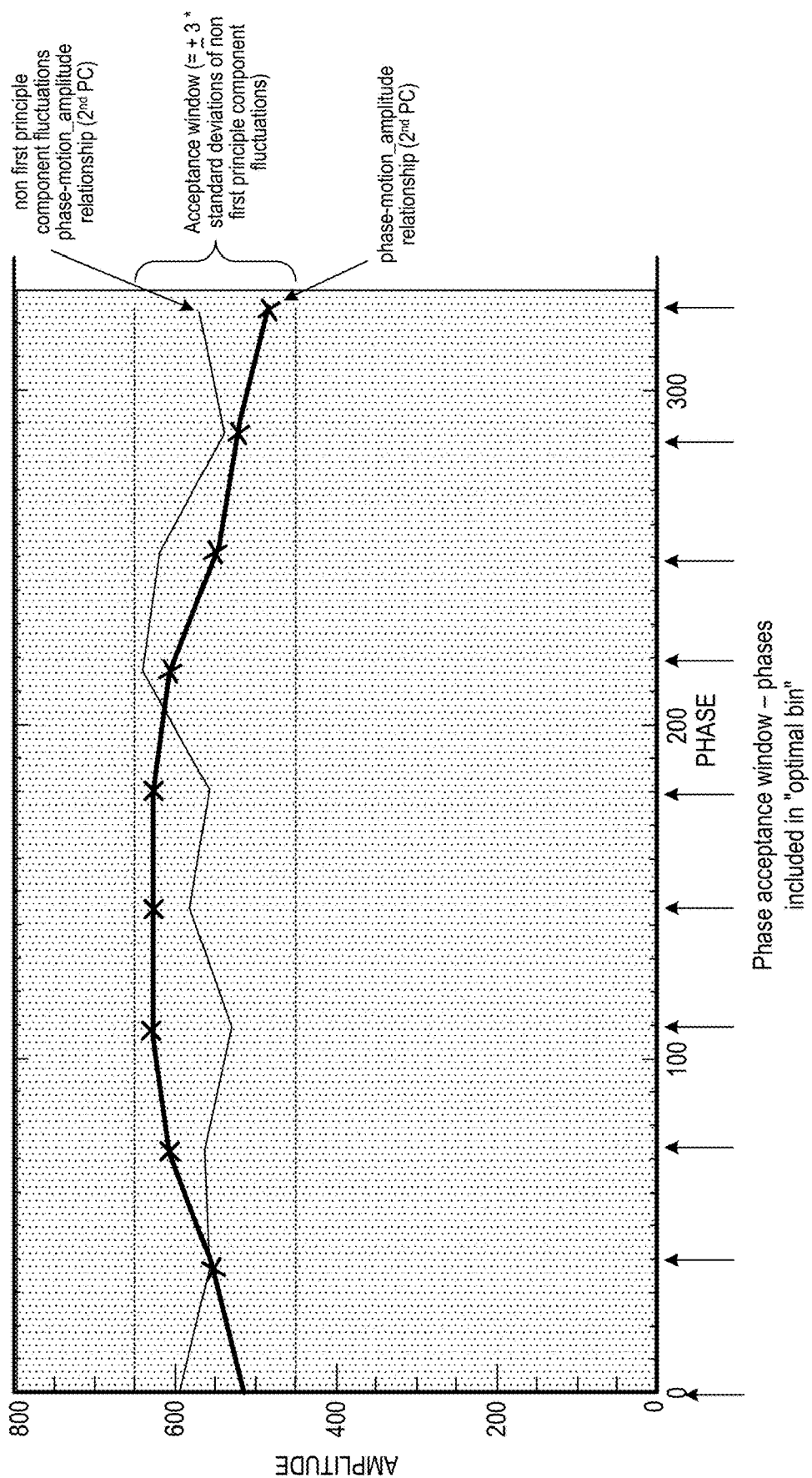
FIG. 12 illustrates a data drive motion curve and optimal phase acceptance window according to one or more embodiments of the present technology.
Figure 13:
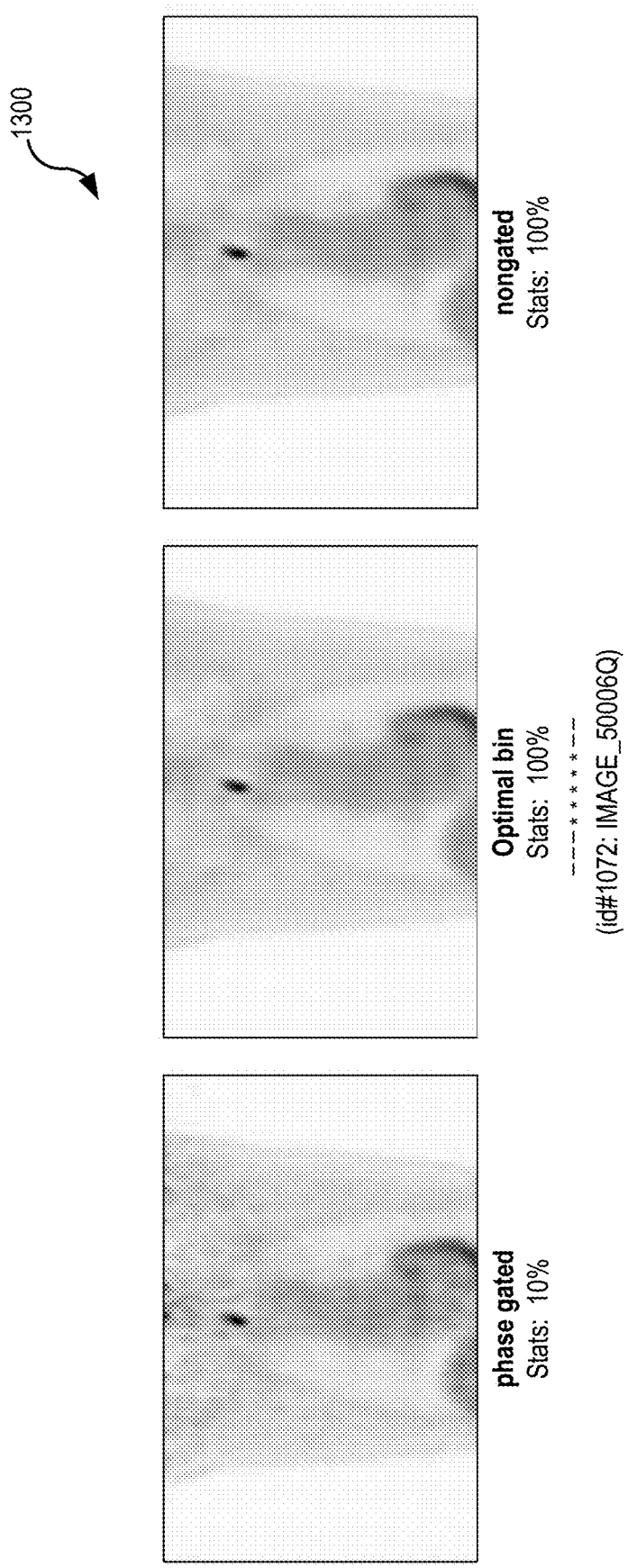
FIG. 13 illustrates images derived from signal binned, optimal binned, and fully binned data in accordance with various embodiments of the present technology.

FIG. 11 illustrates a data driven amplitude phase characterization curve from a patient with non-significant motion in accordance with various embodiments of the present technology. Once the data driven motion curve from the patient is created, an optimal phase acceptance window can be selected as illustrated in FIG. 12, with this case an example of a data sets with 100% of the statistics included in the optimal window. FIG. 13 illustrates images derived from signal binned, optimal binned, and fully binned data in accordance with various embodiments of the present technology.

Figure 14A:
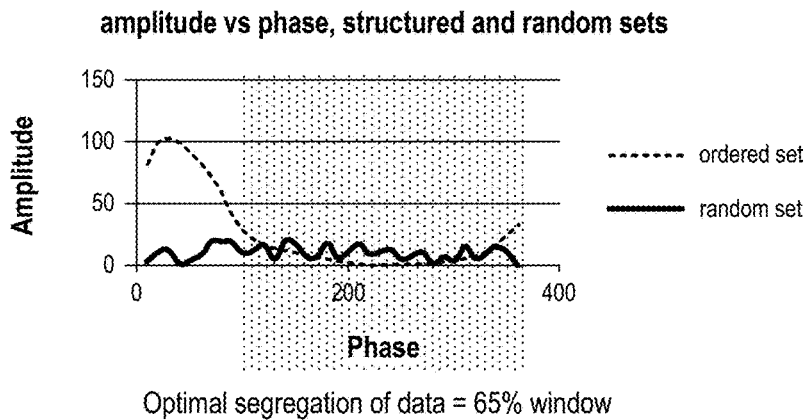
FIGS. 14A-14C illustrate various plots of data sorting determinations based upon phase amplitude characterization in accordance with various embodiments of the present technology.
Figure 14B:
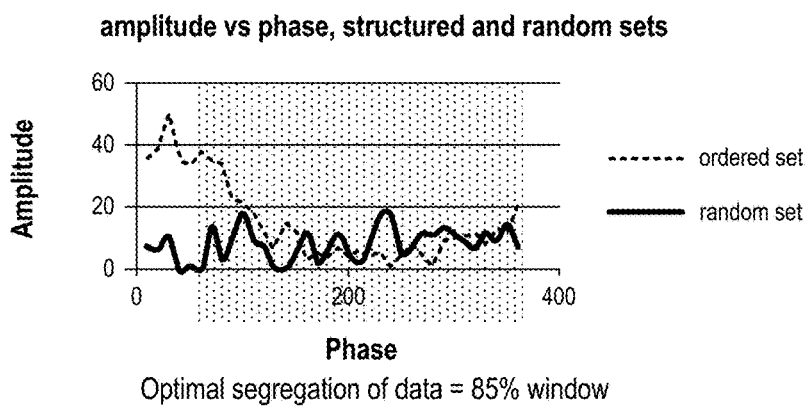
Figure 14C:
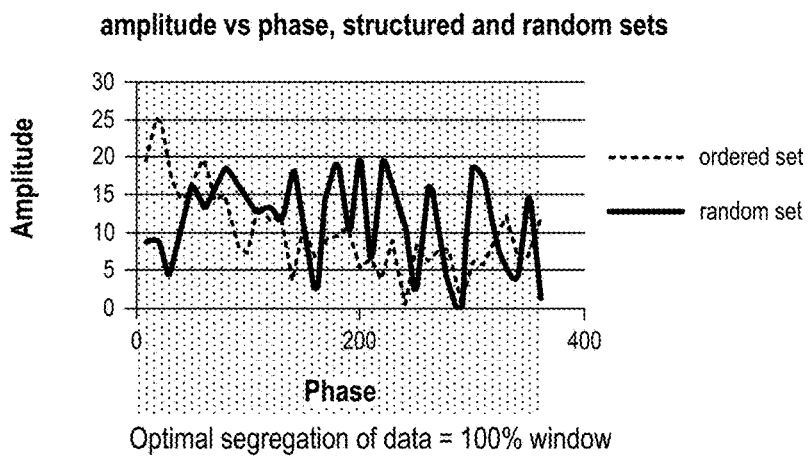

FIGS. 14A-14C illustrate various plots of data sorting determinations based upon phase amplitude characterization in accordance with various embodiments of the present technology. Image data and patient motion characterization can be used in concert to generate a data driven amplitude-based motion characterization. In accordance with various embodiments, these techniques can result in a more robust characterization than those provided by external devices alone. These techniques can be fully automated in various embodiments and allow for amplitude-based gating with data driven motion characterization strategies.

Optimal segregation of data can take place in both pre-reconstructed space and post reconstructed space. Correlative/displacement measurements can take place in reconstructed or pre-reconstructed space. Short time data refers to any subset of total data Optimal final segregation of data will include 1-infiniti bins and may contain 0%-100% of raw data. Gated or optimized segregation of nuclear medicine or PET data may be correlated with matched or unmatched transmission data for attenuation correction, as described in literature.

Exemplary Computer System Overview

Figure 15:
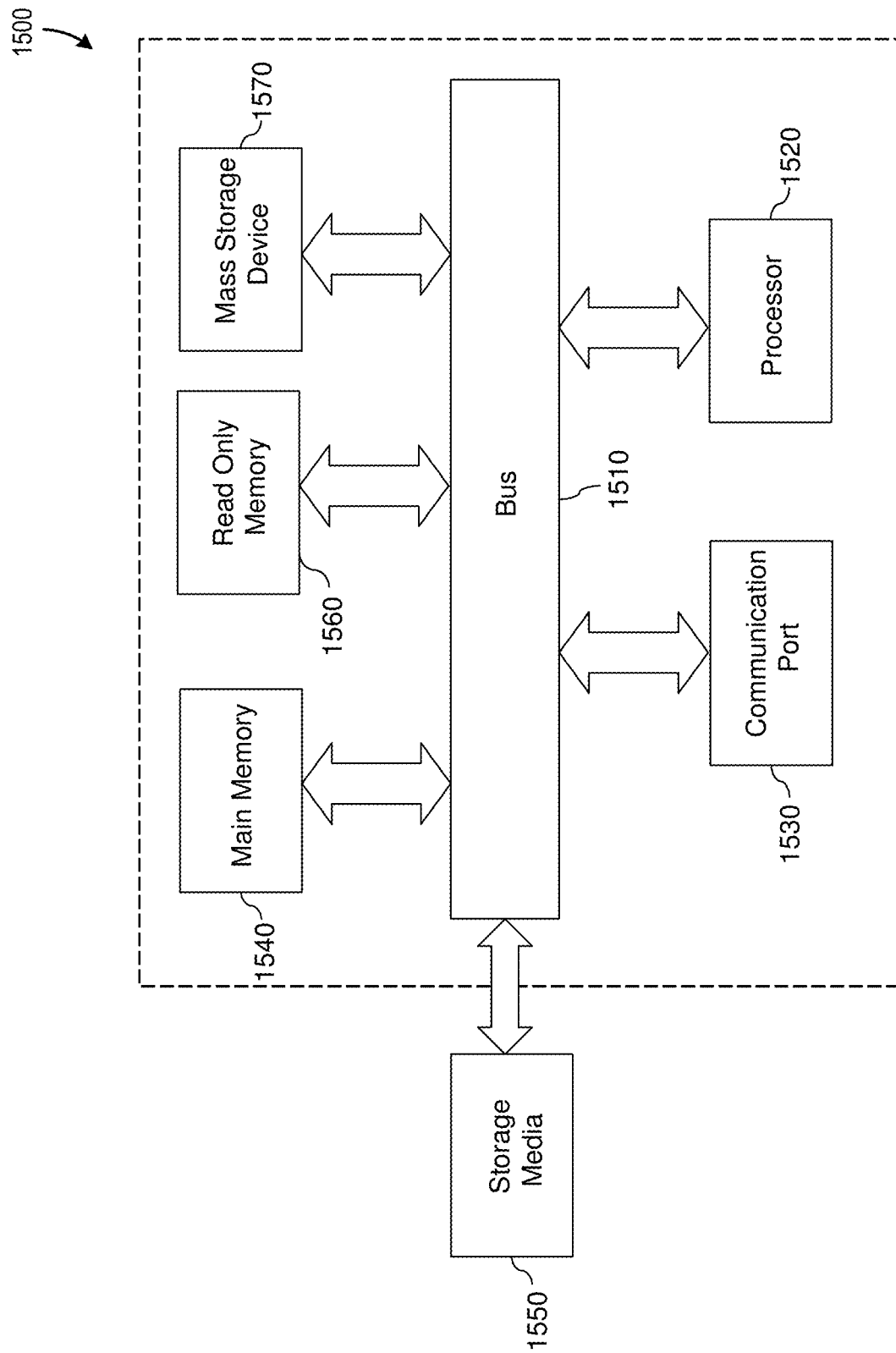
FIG. 15 is a computer system that may be used according to various embodiments of the present technology.

Embodiments of the present invention include various steps and operations, which have been described above. A variety of these steps and operations may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware. As such, FIG. 15 is an example of a computer system 1500 with which embodiments of the present invention may be utilized. According to the present example, the computer system includes a bus 1510, at least one processor 1520, at least one communication port 1530, a main memory 1540, a removable storage media 1550, a read only memory 1560, and a mass storage 1570.

Processor(s) 1520 can be any known processor, such as, but not limited to, Intel® lines of processors; AMD® lines of processors; or Motorola® lines of processors. Communication port(s) 1530 can be any of an RS-232 port for use with a modem-based dialup connection, a 10/100 Ethernet port, or a Gigabit port using copper or fiber. Communication port(s) 1530 may be chosen depending on a network such as a Local Area Network (LAN), Wide Area Network (WAN), or any network to which the computer system 1500 connects.

Main memory 1540 can be Random Access Memory (RAM) or any other dynamic storage device(s) commonly known in the art. Read only memory 1560 can be any static storage device(s) such as Programmable Read Only Memory (PROM) chips for storing static information such as instructions for processor 1520.

Mass storage 1570 can be used to store information and instructions. For example, hard disks such as the Adaptec® family of SCSI drives, an optical disc, an array of disks such as RAID, such as the Adaptec family of RAID drives, or any other mass storage devices may be used.

Bus 1510 communicatively couples processor(s) 1520 with the other memory, storage and communication blocks. Bus 1510 can be a PCI/PCI-X or SCSI based system bus depending on the storage devices used.

Removable storage media 1550 can be any kind of external hard-drives, floppy drives, IOMEGA® Zip Drives, Compact Disc-Read Only Memory (CD-ROM), Compact Disc-Re-Writable (CD-RW), and/or Digital Video Disk-Read Only Memory (DVD-ROM).

The components described above are meant to exemplify some types of possibilities. In no way should the aforementioned examples limit the scope of the invention, as they are only exemplary embodiments.

Embodiments of the present invention may be implemented using a combination of one or more modules. For example, embodiments provide for a graphical user interface generation module to generation one or more graphical user interface screens to convey results/information and take instructions, a general-purpose or special-purpose "communications module" to receive and process various signals, as well as other modules for providing various functionality needed by embodiments of the present invention. Still yet, various embodiments may incorporate two or more of these modules into a single module and/or associate a portion of the functionality of one or more of these modules with a different module.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a computer-readable medium claim, other aspects may likewise be embodied as a computer-readable medium claim, or in other forms, such as being embodied in a means-plus-function claim. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A data-driven gating method comprising:
    acquiring a set of phase-gated medical images collected via a medical imaging procedure on a patient;
    applying a correlative analysis across phases of the set of phase-gated medical images to generate a motion amplitude curve describing an amplitude of motion of the patient during the medical imaging procedure as a function of phase of a periodic motion cycle;
    identifying an acceptance window based on fluctuations in at least one of: phase, and amplitude;
    segregating image data based on the motion amplitude curve relative to the acceptance window; and
    generating one or more medical images based on the segregating of image data.

2. The method of claim 1, wherein the correlative analysis applied is a principal component analysis.

3. The method of claim 2, wherein the principal component analysis of the set of phase gated medical images includes identifying a set of pixels across each medical image in the set of phase gated medical images representing a common point of interest.

4. The method of claim 1, wherein applying the correlative analysis comprises applying a principal component analysis to generate a set of principal components that includes a first principal component and a non-first principal component.

5. The method of claim 4, wherein the motion amplitude curve is based on a weight factor array of the first principal component.

6. The method of claim 5, wherein the acceptance window is identified based on variations in weight factor of fluctuations in the non-first principal component.

7. The method of claim 1, wherein segregating the image data comprises determining an optimal or ideal segregation of the image data.

8. The method of claim 7, wherein determining the optimal segregation of the image data includes analyzing each point on the motion amplitude curve to assess how many other curve data points are included within the acceptance window centered at that point.

9. The method of claim 7, wherein determining the optimal segregation includes:
    classifying image data based on its placement on the motion amplitude curve; and
    combining image data into one or more images based on the classification.

10. The method of claim 1, further comprising characterizing a position of the patient within each medical image in the set of phase gated medical images by using one or more of: a correlative measure, a signal displacement measure, and a frequency-power analysis.

11. A method comprising:
    acquiring a set of phase gated medical images of a patient collected via a medical imaging procedure;
    applying data driven measures to characterize patient motion relative to phase;
    segregating data based on the data driven characterization of patient motion relative to phase to improve image resolution; and
    generating a set of one or more motion gated medical images based on the segregating of the data.

12. The method of claim 11, wherein segregating data comprises segregating data to achieve a desired balance between noise and image resolution.

13. The method of claim 11, wherein patient motion is characterized based on: a center of mass measurement, a gradient displacement, a cost function measured on the gated images, or correlative measures between gated images.

14. The method of claim 11, wherein characterizing the motion of the patient is based on: a principal component analysis, or a frequency power analysis, of the set of phase gated images.

15. The method of claim 11, wherein applying data driven measures to characterize patient motion comprises applying data driven measures to characterize amplitude of patient motion relative to phase.

16. The method of claim 15, wherein characterizing the amplitude of patient motion in the set of phase gated medical images is limited to a subset of pixels or spatial frequencies across each medical image in the set of phase gated medical images representing a target volume signal.

17. The method of claim 11, further comprising:
analyzing phase and amplitude fluctuations to determine optimal, or equal, bin sizes for sorting the set of medical images to maximize image resolution; and
generating the set of gated medical images based on sorting of image data.

18. A system comprising:
a processor;
an image acquisition module, under the control of the processor, configured to acquire a set of medical images of a patient collected via a medical imaging procedure;
a motion characterization module, under the control of the processor, configured to characterize motion of the patient based on the set of medical images;
an optimization module, under the control of the processor, configured to determine bin sizes that improve image resolution of the collected images; and
an image processing module, under the control of the processor, configured to generate a set of gated medical images by: sorting the set of medical images into bins based on the bin sizes, and combining medical images within each of the bins to create the set of gated medical images.

19. The system of claim 18, wherein the motion characterization module applies a principal component analysis to the set of medical images to generate an indication of phase and amplitude fluctuations representing gating of the patient during the medical imaging procedure.

20. The system of claim 18, wherein the motion characterization module is further configured to:
generate an amplitude phase characterization curve; and
characterize a position of the patient within each medical image in the set of medical images by using one or more of: a correlative measure, a signal displacement measure, a principal component analysis, and an interphase frequency power spectrum.

* * * * *